(12) United States Patent
Alasti

(10) Patent No.: US 7,528,272 B2
(45) Date of Patent: May 5, 2009

(54) BIODIESEL PROCESS

(75) Inventor: Perry Alasti, Hopkinton, MA (US)

(73) Assignee: Artisan Industries, Inc., Waltham, MA (US)

( * ) Notice: Subject to any disclaimer, the term of this patent is extended or adjusted under 35 U.S.C. 154(b) by 492 days.

(21) Appl. No.: 11/235,673

(22) Filed: Sep. 26, 2005

(65) Prior Publication Data

US 2006/0074256 A1  Apr. 6, 2006

Related U.S. Application Data

(60) Provisional application No. 60/613,100, filed on Sep. 24, 2004.

(51) Int. Cl.
*C07C 51/43* (2006.01)

(52) U.S. Cl. ..................... 554/174

(58) Field of Classification Search ............. None
See application file for complete search history.

(56) References Cited

U.S. PATENT DOCUMENTS

| | | | |
|---|---|---|---|
| 5,520,708 A | 5/1996 | Johnson et al. | 44/388 |
| 5,525,126 A | 6/1996 | Basu et al. | 44/308 |
| 5,532,392 A | 7/1996 | Gheorghiu | |
| 5,697,986 A | 12/1997 | Haas | 44/308 |
| 5,713,965 A | 2/1998 | Foglia et al. | 44/388 |
| 5,858,169 A | 1/1999 | Rachse et al. | 159/48.1 |
| 6,015,440 A | 1/2000 | Noureddini | 44/388 |
| 6,174,501 B1 | 1/2001 | Noureddini | 422/189 |
| 6,642,399 B2 | 11/2003 | Boocock | 554/167 |
| 6,712,867 B1 | 3/2004 | Boocock | 44/389 |

(Continued)

FOREIGN PATENT DOCUMENTS

EP  1 331 260 A2  7/2003

(Continued)

OTHER PUBLICATIONS

Connemann et al., "Biodiesel in Europe 1998, Biodiesel, Processing and Technologies", International Liquid Biofuels Congress, Jul. 19-22, 1998, pp. 1-15 http://www.biodiesel.org/resources/reportsdatabase/reports/gen/19980722_gen-100.pdf.

(Continued)

*Primary Examiner*—Deborah D Carr
(74) *Attorney, Agent, or Firm*—Weingarten, Schurgin, Gagnebin & Lebovici LLP

(57) ABSTRACT

The present invention provides a biodiesel process capable of yielding a mono-alkyl ester biodiesel. In one embodiment, a process for yielding biodiesel comprises providing a feed stream. Preferably, the feed stream comprises mono-alkyl esters, salts, alcohol and glycerol. The process also comprises substantially separating alcohol from the feed stream to yield a first stream. The first stream comprises mono-alkyl esters, glycerol and salts. A separation of alcohol from the first stream is performed by volatility. Furthermore, the process of the invention comprises substantially separating salts from the first stream to yield a vapor stream. The vapor stream also comprises mono-alkyl esters and glycerol. Separation of salts of the vapor stream is also performed by volatility. Glycerol and mono-alkyl esters of the vapor stream are also substantially separated so as to yield a biodiesel. Preferably, the biodiesel is a fuel grade biodiesel comprising fatty acid mono-alkyl esters.

44 Claims, 6 Drawing Sheets

U.S. PATENT DOCUMENTS

| | | | |
|---|---|---|---|
| 2002/0058827 A1 | 5/2002 | Wollmann et al. | 552/545 |
| 2002/0082434 A1 | 6/2002 | Bonakdar et al. | 552/545 |
| 2003/0229238 A1 | 12/2003 | Fleisher | 554/174 |
| 2004/0034244 A1 | 2/2004 | Bournay et al. | |
| 2004/0231234 A1 | 11/2004 | May et al. | 44/388 |

FOREIGN PATENT DOCUMENTS

| | | |
|---|---|---|
| EP | 1 357 277 A1 | 10/2003 |
| WO | WO 03/083020 A2 | 10/2003 |
| WO | WO 03/087279 A2 | 10/2003 |

OTHER PUBLICATIONS

Khan, "Research into Biodiesel, Kinetics & Catalyst Development", May 17, 2002, pp. 1-39 http://www.cheque.uq.edu.au/ugrad/chee4001/CHEE400102/Adam_Khan_Thesis.pdf Schmidt, "Biodiesel Vehicle Fuel: GHG Reductions, Air Emissions, Supply and Economic Overview", Discussion Paper C3-015, Mar. 11, 2004, pp. 1-20 http://www.climatechangecentral.com/info_centre/discussion_papers/015Biodiesel_Discussion_Paper.pdf.

Westfalia Separator, Inc., "Methyl Ester Processing Line" Westfalia Separator Food Tec, Oils & Fats Processing, Single Separator, p. 1 http://www.wsus.com/en/products/single_separator.html.

Biodiesel Processor Encyclopedis article about Biodiesel Processor pp. 1-3 http://encyclopedia.thefreedictionary.com/biodiesel%20processor.

Levelton Engineering Ltd., (S&T)$^2$ Consultants Inc., Assessment of Biodiesel and Ethanol Diesel Blends, Greenhouse Gas Emissions, Exhaust Emissions, and Policy Issues', Sep. 30, 2002, pp. 1-89 http://www.ghgenius.ca/reports/NRCanBiodiesel.pdf.

Legislative, Thomas., AIM-AG/Agri-Industry Modeling & Analysis Group Economic Feasibility of Producing Biodiesel in Tennessee, Appendix 1. "Congressional Activity, USDA Bioenergy Program, Senate Energy Bill, and EPA Reduced Sulfur Emissions Regulation Provisions" pp. A-1-A-31 http://web.utk.edu/~aimag/pubs/biodiesel.pdf.

Goodrum et al., Biodiesel Production, Biological and Agriculyural Engineering Department, The University of Georgia, pp. 1-33 http://www.georgiaitp.org/PDF/Biodiesel.pdf.

Brevete Biodiesel, http://www.chiminform.home.ro/chim_files/patente_abstract.doc. Copy Not Available.

BIODIESEL PROCESS

CROSS REFERENCE TO RELATED APPLICATIONS

This application claims the priority of U.S. Provisional Application No. 60/613,100 filed Sep. 24, 2004 and entitled, METHOD FOR DESOLVENTIZING AND PURIFYING METHYL ESTER AND GLYCERIN FROM CRUDE BIODIESEL, which is hereby incorporated by reference herein.

BACKGROUND OF THE INVENTION

Biodiesel is a nontoxic and biodegradable fuel that can be used in conventional diesel engines. As a fuel, biodiesel is a renewable alternative to standard petroleum-based diesel fuels. Typically, biodiesel is produced from oils and sources of free fatty acids such as, for example, vegetable oil, animal fat and waste type greases. Biodiesel is usually obtained through an esterification or, preferably, transesterification type process in which triglycerides derived from oil or fat are reacted with alcohol in the presence of a catalyst. In general, the form of biodiesel yielded via a transesterification process can depend on the types of alcohols or solvents employed. For example, often methanol is employed in a transesterification process to obtain a fatty acid methyl ester biodiesel. Alternatively, ethanol can be used in a transesterification process to yield a fatty acid ethyl ester biodiesel. Such biodiesel type esters of fatty acids are commonly referred to as mono-alkyl esters or monoesters. An esterification process can also employ cosolvents such as, for example, methanol and tetrahydrofuran (THF) in order to yield a fatty acid ester biodiesel.

Mono-alkyl esters of fatty acids comprise those fatty acids associated with the oils or fats used in the transesterification process. For naturally occurring oils and fats, the fatty acids of a fatty acid ester biodiesel include, for example, linoleic, stearic, palmitic or oleic acids. The catalyst present within a transesterification process can be basic or acidic in nature. A base catalyzed transesterification process can, for example, use such catalysts as sodium methoxide, potassium hydroxide, sodium hydroxide and combinations thereof. In addition to a mono-alkyl ester biodiesel, a transesterification process yields glycerol, which can be used for cosmetic and pharmaceutical applications. The reaction stoichemitry of a conventional transesterification type process also results in by-products such as, for example, water, excess alcohol, light organics, heavies, free fatty acids and salts.

Primarily, the products from a transesterification process include fatty acid mono-alkyl esters and glycerol. The products also consist of a substantial amount of alcohol, which generally remains in excess due to, for example, the reaction stoichemitry. In order to obtain "fuel grade" biodiesel, fatty acid mono-alkyl esters produced through a transesterification process must be separated from glycerol and any reaction by-products such as heavies, alcohol, light organics, water, free fatty acids and salts. A fuel grade biodiesel is characterized by mono-alkyl esters that satisfy the specifications of the American Society for Testing and Materials (ASTM). Exemplary specifications set by ASTM for evaluation of fatty acid mono-alkyl ester biodiesel include ASTM D 6751.

Commonly, mono-alkyl esters from a transesterification type process are separated from glycerol via conventional means for liquid-liquid type separations such as, for example, a settling vessel. With both a batch or continuous type biodiesel process, such mechanical means of separation are based on the density and solubility differences between glycerol and mono-alkyl esters of fatty acids. In view of the substantial amount of excess alcohol present within fatty acid mono-alkyl esters and glycerol being separated, the physical dimensions of such mechanical separation means can be considerable. Settling vessels can also introduce extended delays in a biodiesel process.

To date, biodiesel processes are generally inefficient and involve both time consuming and maintenance intensive mechanical separations. Such conventional biodiesel processes also tend to suffer from marginal overall biodiesel yields. These shortcomings have impeded the progress of biodiesel as a viable source of alternative energy. The development of a biodiesel fuel as an alternative to standard petroleum-based diesel fuels requires a process that can overcome these shortcomings. Particularly, such a biodiesel process should be capable of continuously producing fuel grade fatty acid mono-alkyl esters from any conventional transesterification process. The process should also minimize the overall number of individual unit operations by providing for efficient and continuous separations.

SUMMARY OF THE INVENTION

The present invention provides a biodiesel process capable of yielding a mono-alkyl ester biodiesel. In one embodiment, a process for yielding biodiesel comprises providing a feed stream. Preferably, the feed stream comprises mono-alkyl esters, salts, alcohol and glycerol. The process also comprises substantially separating alcohol from the feed stream to yield a first stream. The first stream can, for example, comprise mono-alkyl esters, glycerol and salts. Separation of alcohol from the first stream is performed by volatility. Moreover, a process of the invention comprises substantially separating salts from the first stream so as to yield a vapor stream. The vapor stream can, for example, comprise mono-alkyl esters and glycerol. Separation of salts of the vapor stream is also performed by volatility. Glycerol and fatty acid mono-alkyl esters from the vapor stream are then substantially separated to yield a biodiesel. A process of the present invention can overcome the shortcomings of conventional biodiesel processes such as, for example, those described above.

The process of the invention yields a biodiesel comprising mono-alkyl esters of fatty acids such as, for example, linoleic, palmitic, stearic and oleic acids. Preferably, biodiesel from a process of the invention is a fuel grade biodiesel. In another embodiment, the feed stream of the process is obtained from a product stream of an esterification type process, preferably, a transesterification type process. An exemplary esterification type process comprises substantially reacting triglycerides with alcohol to yield a product stream including fatty acid mono-alkyl esters, water, glycerol, salts and alcohol. In addition, an esterification process can employ several types of alcohols, cosolvents or combinations thereof to yield a product stream. For example, methanol and THF can be used in an esterification process so as to yield a product stream. In one embodiment, the process of the invention can comprise substantially separating alcohol and water of the feed stream obtained from a product stream of an esterification process. Alcohol and water are, for example, substantially separated from the obtained feed stream by volatility to yield a first stream.

In one embodiment, the vapor stream yielded from a process of the invention is substantially condensed in order to obtain a liquid stream. The liquid stream comprises mono-alkyl esters and glycerol. Preferably, mono-alkyl esters and glycerol of the liquid stream are substantially separated to yield a biodiesel. Such a substantial separation of glycerol and mono-alkyl esters is, for example, by gravity. In another embodiment, the process of the invention substantially separates fatty acid mono-alkyl esters and glycerol of the vapor stream to yield a liquid stream comprising mono-alkyl esters. For example, such a liquid stream is produced by substantially condensing mono-alkyl esters to produce a biodiesel in, for example, a distillation column. The biodiesel fuel comprises mono-alkyl esters of fatty acids such as, for example, linoleic, palmitic, stearic and oleic acids.

DESCRIPTION OF THE DRAWINGS

Other features and advantages of the invention may also be apparent from the following detailed description thereof, taken in conjunction with the accompanying drawings of which.

DEFINITIONS

Unless otherwise stated, the following definitions provide meaning and examples to terms used herein. Such definitions are also intended to encompass any meaning that may be contemplated or could be appreciated by a person of ordinary skill within the art.

The terms "mono-alkyl ester" or "monoester" and derivations thereof including, for example, mono-alkyl esters, monoesters or esters generally refer to a type of fatty acid ester biodiesel or biodiesel fuel. For example, a fatty acid mono-alkyl ester biodiesel comprises fatty acids such as oleic, stearic, linoleic or palmitic acids as well as any sort of combinations of these fatty acids.

DETAILED DESCRIPTION OF THE INVENTION

The present invention provides a biodiesel process capable of yielding mono-alkyl ester biodiesel. In one embodiment, the process of the invention yields biodiesel comprising fatty acid mono-alkyl esters. Fatty acid mono-alkyl esters comprise fatty acids such as, for example, linoleic, stearic, palmitic and oleic acids. The process of the invention can also produce a fuel grade fatty acid mono-alkyl ester biodiesel. Preferably, a process of the present invention is substantially continuous. A process of the invention produces a generally continuous yield of mono-alkyl ester biodiesel from such sources of oils and fats as, for example, animal fat, waste type grease, vegetable oil or algae.

Figure 1:
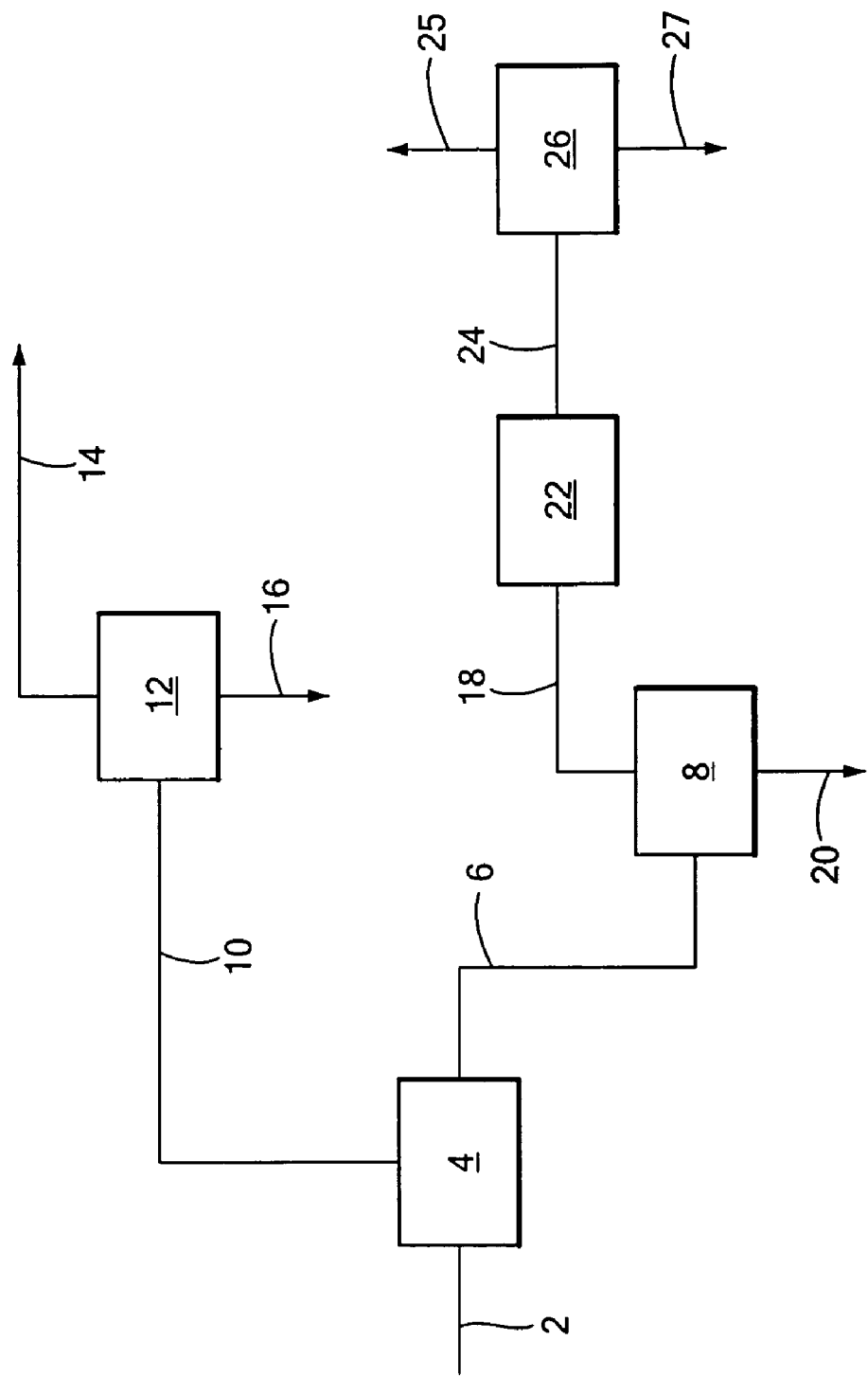
FIG. 1 is a representation of a process of the invention for yielding biodiesel.

FIG. 1 is a representation of a process of the invention for yielding biodiesel. FIG. 1 shows a feed stream 2 that can comprise, for example, salts, alcohol, glycerol and mono-alkyl esters. The feed stream is obtained from an esterification type process such as, for example, a transesterification process. An exemplary esterification process comprises substantially reacting triglycerides with alcohol so as to yield glycerol and mono-alkyl esters. Moreover, an esterification process results in reaction by-products such as, for example, heavies, salts, excess alcohol, free fatty acids and water, which can also be present in the feed stream 2. In one embodiment, the extents of reaction via esterification can vary the composition of the feed stream 2, which is obtained therefrom.

Triglycerides are substantially reacted with alcohol in a conventional esterification process to obtain the feed stream 2. The extents of reaction by esterification can vary given such factors as, for example, reaction stoichemitry and conditions. Moreover, the composition of the feed stream can vary depending on the type of catalyst used for esterification. A feed stream 2 can be obtained from any conventional esterification processes. Exemplary esterification processes are described by U.S. Pat. Nos. 6,855,838, 6,822,105, 6,768,015, 6,712,867, 6,398,707 or 6,642,399, which are hereby incorporated by reference herein.

As shown, the feed stream 2 of FIG. 1 is introduced to a first separation means 4. The separation means 4 substantially separates alcohol from the feed stream 2 to yield a first stream 6 featuring, for example, glycerol, salts and mono-alkyl esters. Preferably, the process of FIG. 1 comprises a preheating means in order to preheat the feed stream 2 prior to introduction to the first separation means 4. The separation means substantially separates alcohol present in the feed stream by volatility. In general, a separation by volatility is based on differences in vapor pressure. For example, the first separation means can be used to vaporize a portion of alcohol from the feed stream 2 to yield the first stream. A portion of alcohol in the feed stream is vaporized therefrom given its high vapor pressure as compared to, for example, mono-alkyl esters, glycerol and salts.

In one embodiment, the first separation means 4 can be a conventional type of thermal-based unit operation such as, for example, an evaporator. Exemplary evaporator types for the first separation means 4 can include forced-circulation, rising film and falling film evaporators. For example, the first separation means can be an agitated-film evaporator. Preferably, a process of the invention comprises a substantially horizontal, thin or wiped rotary blade evaporator. For example, such a substantially horizontal, thin or wiped rotary blade evaporator is a ROTOTHERM (Artisan Industries Incorporated of Waltham, Mass. 02451) evaporator. Examples of conventional agitated-film evaporators are described by U.S. Pat. Nos. 3,561,517, 3,891,495, 3,985,606, 4,054,485, 3,678,983, 3,695,327, 3,633,645 or 4,093,479, which are hereby incorporated by reference herein.

As described above, the first separation means 4 of FIG. 1 separates alcohol from the feed stream 2, which is provided thereto. The extent of alcohol separation from the feed stream 2 can vary depending on several factors. For example, the design, type, orientation or operating conditions of the first separation means 4 can affect the extent of separation of alcohol. Such factors can also be modified or adjusted in order to influence the overall quantity or quality of a biodiesel produced by a process of the invention. In another embodiment, the extent of alcohol separation is adjusted as the process of the invention is being carried out. Preferably, alcohol is separated from the feed stream 2 in an evaporator such as, for example, an agitated-film evaporator.

In another embodiment, the first separation means 4 also substantially separates water present in the feed stream 2 so as to yield the first stream 6. As shown, the first stream 6 exits the first separation means 4 and is then introduced to a second separation means 8. FIG. 1 shows a vapor stream 10 exiting the separation means 4 and entering a column 12. The column 12 can be any conventional type of column such as a distillation column. Exemplary distillation columns include tray or packed columns that are liquid of vapor feed. The column 12 can also be a batch or continuous type column. Preferably, the column 12 is a distillation column used to substantially separate alcohol from water present in the vapor stream 10. The column 12 also comprises conventional components such as, for example, reflux drums, condensers, reboilers or any combination thereof.

FIG. 1 shows the column 12 receiving the vapor stream 10 comprising, for example, alcohol and water. In one embodiment, alcohol is enriched in a column rectifying section so as to exit the column 12 in an overhead vapor stream 14. Moreover, water is stripped in a stripping section of the column so as to depart the column in a bottoms stream 16. The overhead vapor stream 14 is condensed via a condenser and a portion thereof refluxed to the column 12. Similarly, a portion of the bottoms stream 16 is reboiled and then returned to the column. Preferably, alcohol in the overhead vapor stream 14 is recycled in order to carry out, for example, the esterification process. In general, water in the bottoms stream 16 is sent to waste water treatment.

The extent of alcohol separation from water in the vapor stream 10 can vary depending on several factors. For example, the type of distillation column 12 can influence the extent of separation of alcohol from water to yield the overhead vapor 14 and bottoms stream 16, respectively. The operating conditions for the column 12 can also affect the extent of separation. Such factors can also be modified or adjusted so as to influence, for example, the purity of alcohol in the overhead vapor stream 14 for recycling as described above. In one embodiment, the extent of separation in the distillation column 12 can be adjusted as the process of the invention is being carried out.

FIG. 1 also shows the first stream 6 introduced to the second separation means 8. Preferably, the separation means 8 is any conventional type of thermal-based unit operation such as, for example, an evaporator. Exemplary evaporator types for the second separation means 8 can include forced-circulation, rising film and falling film evaporators. For example, the separation means 8 can be an agitated-film evaporator. Preferably, a process of the invention comprises a substantially horizontal, thin or wiped rotary blade evaporator. For example, such a substantially horizontal, thin or wiped rotary blade evaporator is a ROTOTHERM (Artisan Industries Incorporated of Waltham, Mass. 02451) evaporator. Examples of conventional agitated-film evaporators are described by U.S. Pat. Nos. 3,561,517, 3,891,495, 3,985,606, 4,054,485, 3,678,983, 3,695,327, 3,633,645 or 4,093,479, which are hereby incorporated by reference herein.

As shown in FIG. 1, the separation means 8 substantially separates salts from the first stream 6 to yield a vapor stream 18 comprising mono-alkyl esters and glycerol. In one embodiment, separation of salts from the first stream is by volatility. As described above, separation by volatility is based on differences in vapor pressure. For example, the means 8 is used to vaporize a portion of mono-alkyl esters and glycerol from the first stream 6 to yield the vapor stream 18. A portion of mono-alkyl esters and glycerol in the first stream 6 are vaporized therefrom given the high vapor pressure of esters and glycerol as compared to, for example, salts, which are essentially non-volatile.

The extent of separation of salts from the first stream 6 can vary depending on several factors. For example, the design, type, orientation or operating conditions of the second separation means 8 can affect the extent of separation of salts present in the first stream 6. Such factors can be modified or adjusted so as to influence the overall quantity or quality of a biodiesel produced by a process of the invention. In general, the extent of salts separation can be adjusted while the process of the invention is carried out. Preferably, salts are substantially separated from the stream 6 within an evaporator such as, for example, an agitated-film evaporator. The resulting vapor stream 18 comprises mono-alkyl esters and glycerol.

Salts substantially separated from the first stream comprise a residue stream 20. The residue stream 20 is properly disposed of by any suitable means. Typically, the residue stream comprises a substantial portion of heavies that can be present in the feed stream 2. Preferably, fatty acid mono-alkyl esters and glycerol of the vapor stream are substantially separated so as to yield a biodiesel.

In one embodiment, the vapor stream 18 is introduced to a condenser 22 to perform condensing thereof. Preferably, the vapor stream 18 is substantially condensed by the condenser. For example, a portion of the vapor stream is condensed prior to separation of glycerol from mono-alkyl esters so as to yield biodiesel. The condenser 22 can be any conventional type of condenser such as, for example, a vertical or horizontal type condenser. The extent of condensation of the vapor stream 18 can vary depending on several factors such as, for example, the type of condenser 22. Moreover, the cooling media and operating conditions of the condenser 22 can also affect the extent of condensation.

Such factors relating to the process of the invention can also be modified or adjusted in order to influence, for example, the overall quality of biodiesel. In one embodiment, the extent of condensation in the condenser 22 is adjusted as the process of the invention is performed in, for example, a substantially continuous manner. FIG. 1 also shows the condenser 22 yields a liquid stream 24 comprising fatty acid mono-alkyl esters and glycerol. Preferably, fatty acid mono-alkyl esters and glycerol are separated by gravity to yield biodiesel. A portion of mono-alkyl esters in the liquid stream 24 are separated therefrom given the density and solubility differences of esters as compared to glycerol. Such a separation by gravity so as to yield a mono-alkyl ester biodiesel can be performed by any suitable means.

For example, separating mono-alkyl esters from glycerol can occur in any suitable process operation such as, for example, sedimentation, centrifugation, membrane separation or any types of combinations thereof. FIG. 1 also shows condensed mono-alkyl esters substantially separated from glycerol via a centrifuge 26. For example, mono-alkyl esters exit the centrifuge 26 in a yield stream 25 and glycerol in a residual stream 27. The centrifuge 26 can be any type of conventional centrifuge such as a tubular bowl or decanter type centrifuge. The centrifuge 26 can further be of any suitable orientation such as generally horizontal or vertical. Moreover, the extent of separation of mono-alkyl esters from glycerol can vary depending on several factors such as, for example, the type of and operating conditions for the centrifuge. In addition, substantially separated glycerol from the centrifuge 26 can be used for any suitable applications such as, for example, cosmetic and pharmaceutical applications.

Figure 2:
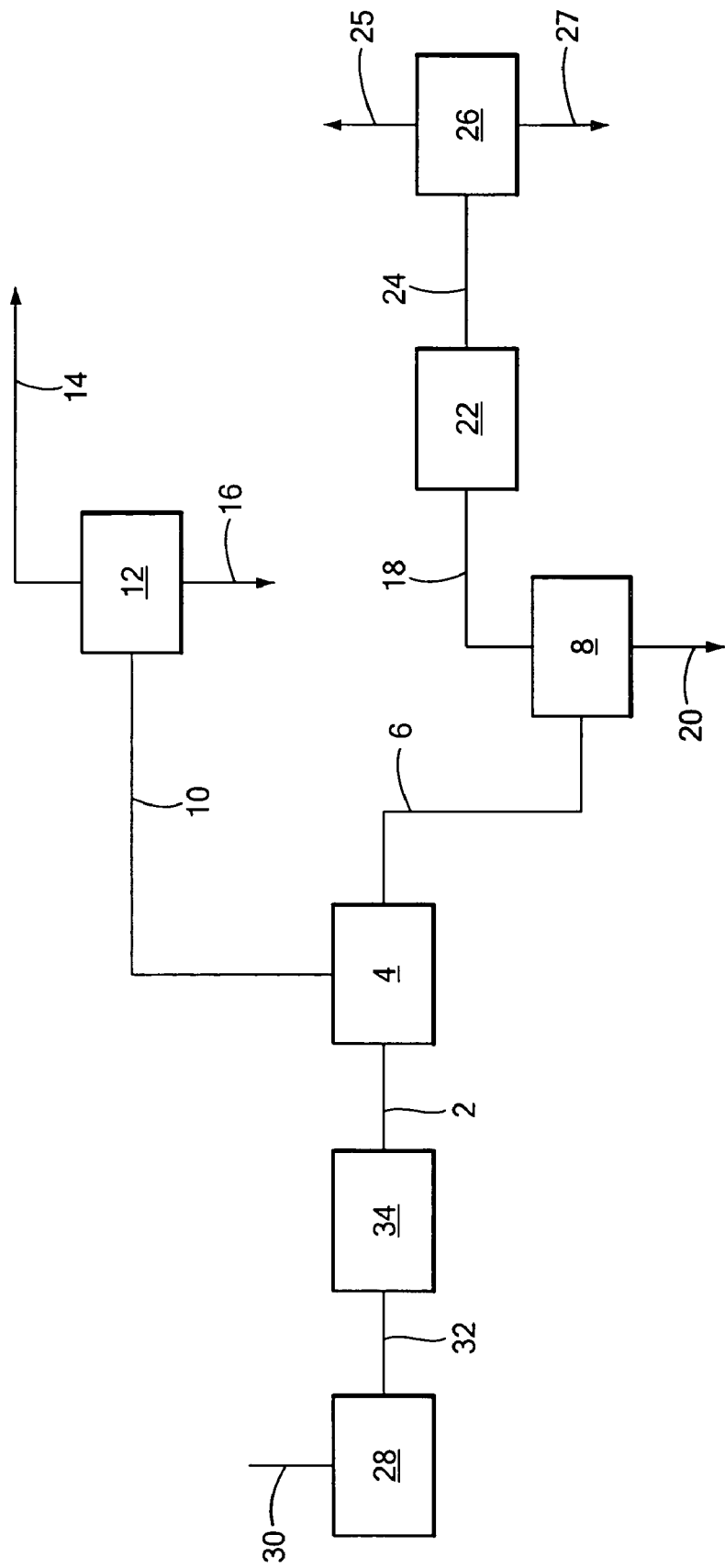
FIG. 2 is a representation of a process of the invention for yielding biodiesel.

FIG. 2 also shows a representation of a process of the invention for yielding biodiesel. Particularly, FIG. 2 shows a process comprising a reactor 28. In one embodiment, the reactor 28 can be used to carry out an esterification type process such as a transesterification process. For example, the reactor 28 is used for a transesterification type process in which a feed source of triglycerides is introduced thereto. Preferably, the feed source for the transesterification process comprises algae vegetable oil, animal fat, waste type greases or combinations thereof. The feed source is provided to the reactor in a feed 30. The feed 30 for the process of the invention comprises a feed source of triglycerides and alcohol. Alternatively, several types of alcohols, cosolvents or any combination thereof can also be present in the feed 30 so as to yield a product stream via esterification. Generally, the product stream 32 exiting from the reactor varies depending on the composition of the feed 30.

In one embodiment, the feed 30 can comprise alcohol such as methanol to yield methyl esters. Alternatively, ethanol can be used in the feed 30 to yield ethyl esters. As described above, a process of the invention can also use different types of alcohols, cosolvents or any combinations thereof in the feed 30 to yield mono-alkyl esters comprising fatty acids such as, for example, stearic, linoleic, palmitic and oleic acid. The fatty acids of mono-alkyl esters can also vary based on the feed source. As shown in FIG. 2, the feed 30 is provided to the reactor 28 such that available triglycerides are substantially reacted with alcohol via an esterification process. The process of esterification can occur in the presence of a catalyst. The catalyst can be basic or acidic in nature such as, for example, potassium hydroxide, sodium methoxide, sodium hydroxide and any suitable combinations thereof.

As described above, triglycerides from the feed source are substantially reacted with alcohol in the reactor 28 to yield a product stream 32. The product stream can comprise glycerol and mono-alkyl esters. Furthermore, the esterification process from which the product stream is yielded can produce reaction by-products such as, for example, heavies, salts, free fatty acids, excess alcohol and water. The extent of esterification within the reactor 28 can also vary the composition of the feed stream 2 obtained from the product stream 32. For example, the stream 2 can comprise alcohol, water, heavies, free fatty acids, mono-alkyl esters, salts and glycerol. The extent of esterification can also vary given such factors as reaction stoichemitry and conditions.

In one embodiment, the reactor 28 can be any given type of conventional reactor suitable for carrying out an esterification process. Exemplary reactors can include, for example, tubular, fixed bed, stirred tank and fluid bed reactors. A process of the invention can also feature a plurality of reactors in any type of configuration such as, for example, in parallel or series. A process of the invention can optionally separate water present in the feed 30 prior to esterification by any suitable means. For example, such means can be a conventional evaporator. Exemplary types of evaporators for substantially separating water in the feed 30 from a feed source include forced-circulation, rising film and falling film evaporators. Preferably, the evaporator is an agitated-film evaporator such as a ROTOTHERM (Artisan Industries Incorporated of Waltham, Mass. 02451) evaporator. The extent of water present in the feed 30 depends on the feed source used.

As shown, the process of FIG. 2 comprises an optional preheating means 34 in order to preheat the feed stream 2 prior to introduction to the first separation means 4. The feed stream obtained from the product stream 32 of the reactor 28 can have a composition that varies based on the type, design and operating conditions of the reactor 28. Such factors can also be modified or adjusted so as to influence the overall quantity or quality of the feed stream. In one embodiment, for example, the extent of esterification can be adjusted as a process of the invention is continuously carried out. The orientation of the reactor 28 can also affect the extent of reaction. Moreover, as described above, the type of catalyst, alcohols, solvents, feed source and combinations thereof can affect the composition of the stream 2.

FIG. 2 also shows the various aspects of the process in FIG. 1. The process of FIG. 2 can also include or otherwise incorporate any suitable variations such as, for example, those generally described above. In one embodiment, the feed stream 2 is introduced to the first separation means 4. The separation means 4 substantially separates alcohol from the feed stream 2 so as to yield a first stream 6 featuring, for example, glycerol, salts and mono-alkyl esters. The separation means substantially separates alcohol from the feed stream 2 by volatility. For example, the first separation means is used in order to vaporize a portion of alcohol from the feed stream 2 to yield the first stream 6. The separation means 4 also substantially separates water present in the feed stream 2.

As shown, the first stream 6 exits the first separation means 4 and is then introduced to a second separation means 8. FIG. 2 shows a vapor stream 10 exiting the separation means 4 and entering a column 12. The column 12 can be any conventional type of column such as a distillation column. Preferably, the column 12 is a distillation column used to substantially separate alcohol from water present in the vapor stream 10. For example, alcohol departs from the column 12 in an overhead vapor stream 14 as water exits therefrom in a bottoms stream 16.

FIG. 2 also shows the first stream 6 introduced to the second separation means 8. The separation means 8 substantially separates salts from the first stream 6 to yield a vapor stream 18 comprising mono-alkyl esters and glycerol. In one embodiment, separation of salts from the first stream 6 is by volatility. Salts substantially separated from the first stream 6 comprise a residue stream 20. The residue stream 20 is properly disposed of by any suitable means. Typically, the residue stream comprises a substantial portion of heavies that can be present in the feed stream 2. Mono-alkyl esters and glycerol of the vapor stream 18 are substantially separated so as to yield a biodiesel.

In one embodiment, the vapor stream 18 is introduced to a condenser 22 to perform condensing thereof. Preferably, the vapor stream 18 is substantially condensed by the condenser 22. For example, a portion of the vapor stream is condensed prior to separation of glycerol from mono-alkyl esters so as to yield biodiesel. FIG. 2 also shows the condenser 22 yields a liquid stream 24 comprising fatty acid mono-alkyl esters and glycerol. Preferably, mono-alkyl esters and glycerol are then separated by gravity to yield biodiesel. A portion of mono-alkyl esters in the liquid stream 24 are separated therefrom given the density and solubility differences of esters as compared to glycerol.

As shown in FIG. 2, substantially condensed fatty acid mono-alkyl esters are separated from glycerol in a centrifuge 26. For example, mono-alkyl esters exit the centrifuge in a yield stream 25 and glycerol in a residual stream 27. Preferably, the process of FIG. 2 is substantially continuous and capable of producing fuel grade biodiesel.

Figure 3:
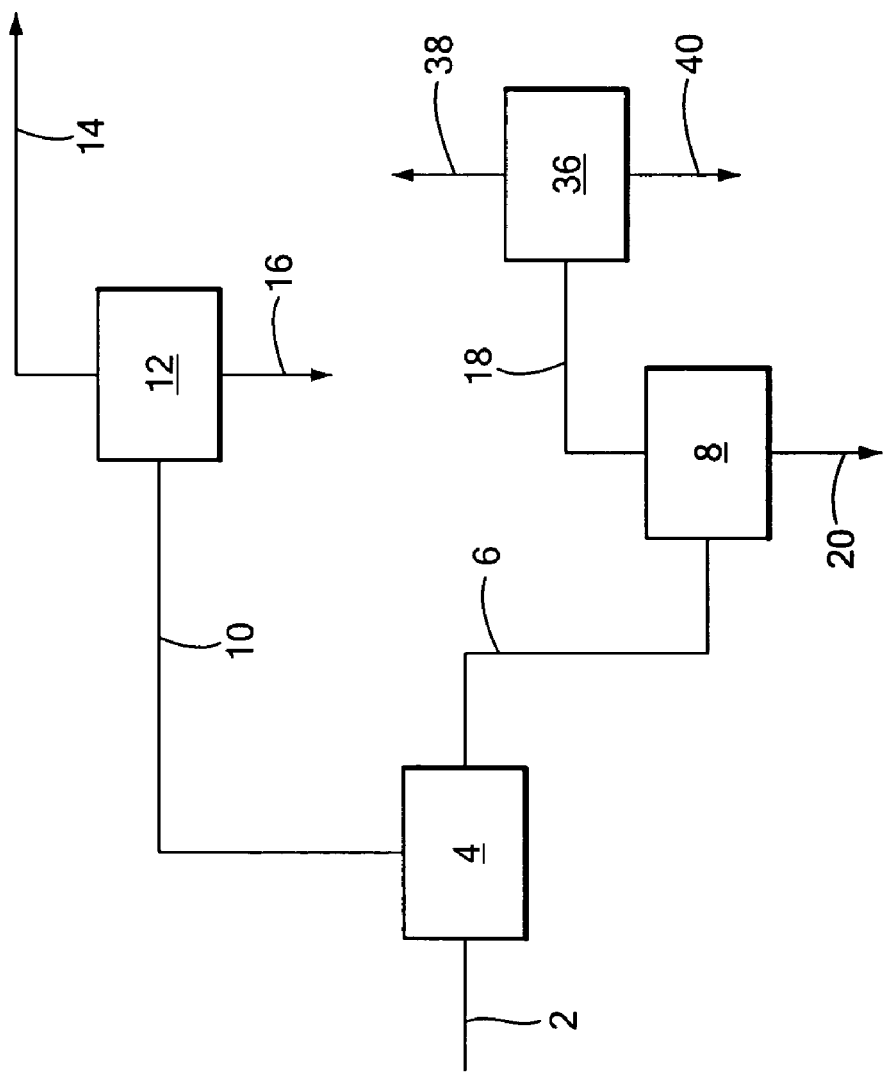
FIG. 3 is a representation of a process of the invention for yielding biodiesel.

FIG. 3 is a representation of a process of the invention for yielding biodiesel. FIG. 3 also features several of the various aspects of the processes in FIGS. 1 and 2. The process of FIG. 3 can include or incorporate any suitable variations such as, for example, those generally described above. In one embodiment, the feed stream 2 is obtained from any conventional esterification type process. The feed stream 2 is then introduced into the first separation means 4. The first separation means 4 substantially separates alcohol and water from the feed stream 2 to yield a first stream 6 comprising, for example, glycerol, salts and mono-alkyl esters. The separation means substantially separates alcohol and water from the feed stream by volatility. For example, the first separation means 4 is used in order to vaporize a portion of alcohol and water from the feed stream 2 to yield the first stream 6. Portions of alcohol and water in the feed stream are vaporized therefrom given the high vapor pressure of each as compared to, for example, mono-alkyl esters, glycerol and salts.

The process of FIG. 3 can optionally include a preheating means so as to preheat the feed stream 2 prior to introduction to the first separation means 4. As shown, the first stream 6 exits the first separation means 4 and is then introduced to a second separation means 8. FIG. 3 also shows a vapor stream 10 exiting the separation means 4 and entering a column 12. The column 12 can be any conventional type of column such as a distillation column. Preferably, the column 12 is a distillation column used to substantially separate alcohol from water present in the vapor stream 10. For example, alcohol departs from the column in an overhead vapor stream 14 as water exits therefrom in a bottoms stream 16.

FIG. 3 also shows the first stream 6 introduced to the second separation means 8. The separation means 8 substantially separates salts from the first stream 6 to yield a vapor stream 18 comprising mono-alkyl esters and glycerol. In one embodiment, separation of salts from the first stream 6 is by volatility. Salts substantially separated from the first stream 6 comprise a residue stream 20. The residue stream 20 is properly disposed of by any suitable means. Typically, the residue stream 20 comprises a substantial portion of heavies that can be present in the feed stream 2.

In one embodiment, the vapor stream 18 can be introduced to a column 36 such as a conventional type of distillation column. Exemplary distillation columns include tray or packed columns that are liquid of vapor feed. The column 36 can also be a batch or continuous type column. Preferably, the column 36 is used to separate glycerol and fatty acid mono-alkyl esters present in the vapor stream by substantially condensing mono-alkyl esters. In general, mono-alkyl esters from the vapor stream are substantially condensed during separation from glycerol in the column 36. The column 36 also comprises conventional components such as, for example, reflux drums, condensers, reboilers or any combinations thereof. The column 36 can also feature any suitable reflux ratio.

FIG. 3 shows the column 36 receiving the vapor stream 18 comprising, for example, glycerol and mono-alkyl esters. In one embodiment, glycerol can be enriched within a column rectifying section so as to exit the column 36 in an overhead vapor stream 38. Moreover, mono-alkyl esters can be stripped in a stripping section of the column so as to depart the column 36 in a bottoms stream 40. The overhead vapor stream 38 is condensed and a portion thereof refluxed to the column 36. Similarly, a portion of the bottoms stream 40 is also reboiled and then returned to the column 36.

The extent of glycerol separated from fatty acid mono-alkyl esters in the vapor stream 18 can vary depending on several factors such as the type of column 36. Moreover, the operating conditions of the column can influence the extent of separation of glycerol from mono-alkyl esters. Such factors can be modified or adjusted to influence, for example, the overall quantity or quality of biodiesel produced by the process shown in FIG. 3. Preferably, the extent of separation in the distillation column 36 can be adjusted as the process of the invention is carried out in a substantially continuous manner.

Figure 4:
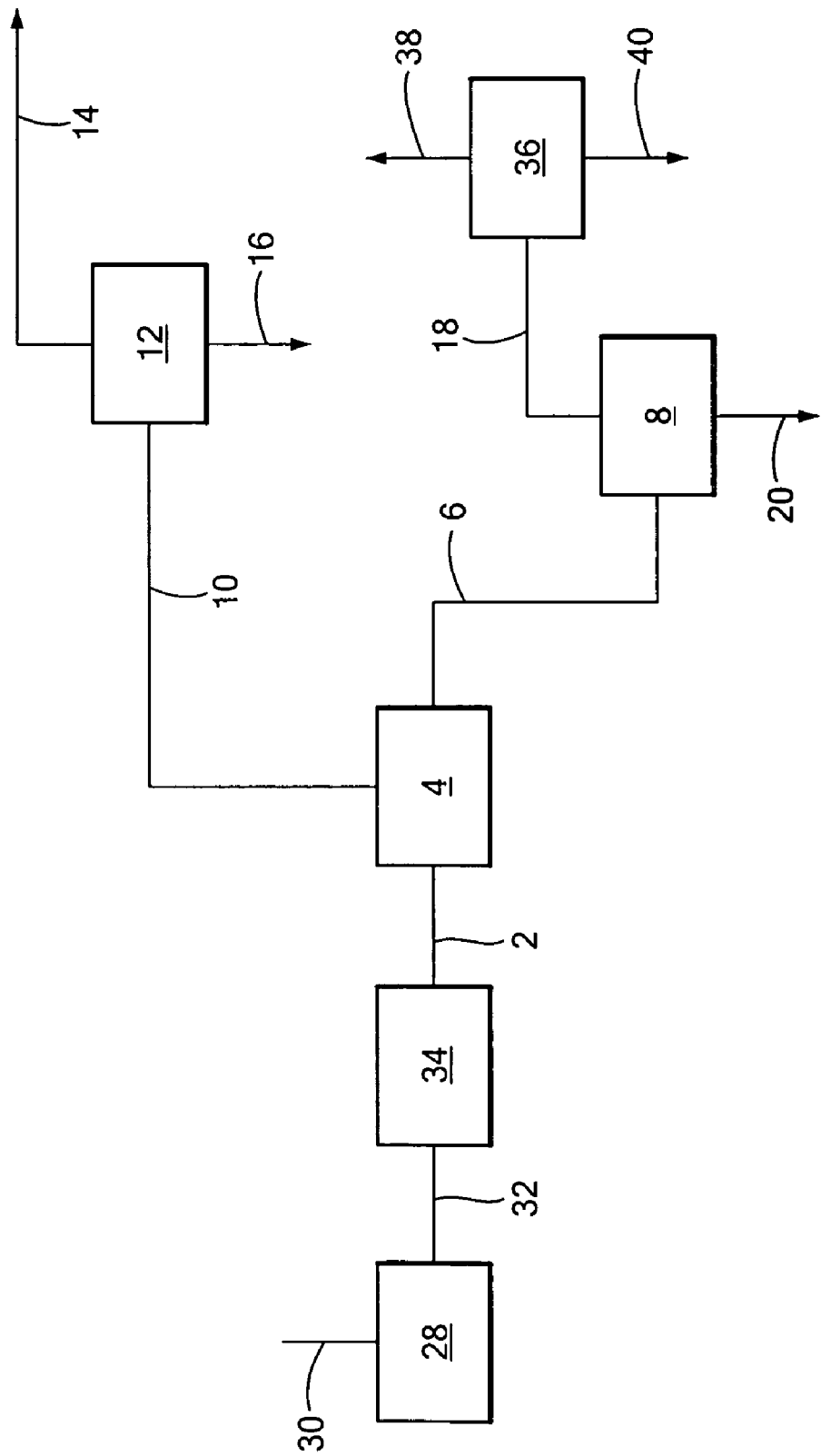
FIG. 4 is a representation of a process of the invention for yielding biodiesel.

FIG. 4 is a representation of a process of the invention for yielding biodiesel. FIG. 4 also features several of the aspects of the processes in FIGS. 1, 2 and 3. The process of FIG. 4 can include or incorporate any suitable variations such as, for example, those described above. Particularly, FIG. 4 shows a process comprising a reactor 28. In one embodiment, the reactor 28 can be used so as to carry out an esterification type process such as, for example, a transesterification type process. For example, the reactor can be used for a transesterification type process in which a feed source of triglycerides is provided thereto such as described above. The feed source is provided to the reactor 28 in a feed 30.

As described above, a feed source comprising triglycerides is substantially reacted with alcohol in the reactor 28 to yield a product stream 32. The product stream comprises glycerol and mono-alkyl esters. In addition, the product stream also includes alcohol, water, heavies, free fatty acids and salts. The feed stream 2 is obtained from the product stream 32. As shown, the process of FIG. 4 comprises an optional preheating means 34 in order to preheat the feed stream 2 prior to introduction to the first separation means 4.

The feed stream 2 is introduced to the first separation means 4. The first separation means 4 substantially separates alcohol and water from the feed stream 2 to yield a first stream 6 comprising, for example, glycerol, salts and fatty acid mono-alkyl esters. The separation means 4 substantially separates alcohol and water from the feed stream by volatility. For example, the first separation means is used in order to vaporize a portion of alcohol and water from the feed stream 2 to yield the first stream 6.

In addition, the first stream 6 exits the first separation means 4 and is then introduced to a second separation means 8. FIG. 4 shows a vapor stream 10 exiting the separation means 4 and entering a column 12. The column 12 can be any conventional type of column such as a distillation column. Preferably, the column 12 is a distillation column used to substantially separate alcohol from water present in the vapor stream 10. For example, alcohol departs from the column in an overhead vapor stream 14 as water exits therefrom in a bottoms stream 16.

FIG. 4 also shows the first stream 6 introduced to the second separation means 8. The separation means 8 substantially separates salts from the first stream 6 to yield a vapor stream 18 comprising mono-alkyl esters and glycerol. In one embodiment, separation of salts from the first stream 6 is by volatility. Salts substantially separated from the first stream 6 comprise a residue stream 20. The residue stream 20 is properly disposed of by any suitable means. Typically, the residue stream 20 comprises a substantial portion of heavies that can be present in the feed stream 2.

In one embodiment, the vapor stream 18 can be introduced to a column 36 such as a conventional type of distillation column. Exemplary distillation columns include tray or packed columns that are liquid of vapor feed. The column 36 can also be a batch or continuous type column. Preferably, the column 36 is used to substantially separate glycerol and mono-alkyl esters present in the vapor stream 18. As described above, the column 36 comprises conventional components such as, for example, condensers, reflux drums, reboilers or any combinations thereof. The column 36 can also feature any suitable reflux ratio.

FIG. 4 shows the column 36 receiving the vapor stream 18 comprising, for example, glycerol and mono-alkyl esters. In one embodiment, glycerol exits the column 36 in an overhead vapor stream 38. Moreover, mono-alkyl esters depart the column 36 in a bottoms stream 40, which is a liquid stream. Preferably, mono-alkyl esters and glycerol present in the overhead vapor stream 18 are substantially separated to yield the bottoms stream. As described above, such a separation is performed by substantially condensing mono-alkyl esters in the column 36. In FIG. 4, the overhead vapor stream is condensed via a condenser and a portion thereof refluxed to the column so as to minimize carry over of biodiesel into the glycerol stream.

The examples herein are provided to illustrate advantages of the invention that have not been previously described and to further assist a person of ordinary skill in the art with using a process of the invention. The examples herein can include or incorporate the variations or inventive embodiments as described above. The embodiments that are described above also can each include or otherwise incorporate the variations of any or all other embodiments herein. The examples are not intended in any way to otherwise limit or narrow the disclosure or scope thereof as provided herein.

EXAMPLE I

Figure 5:
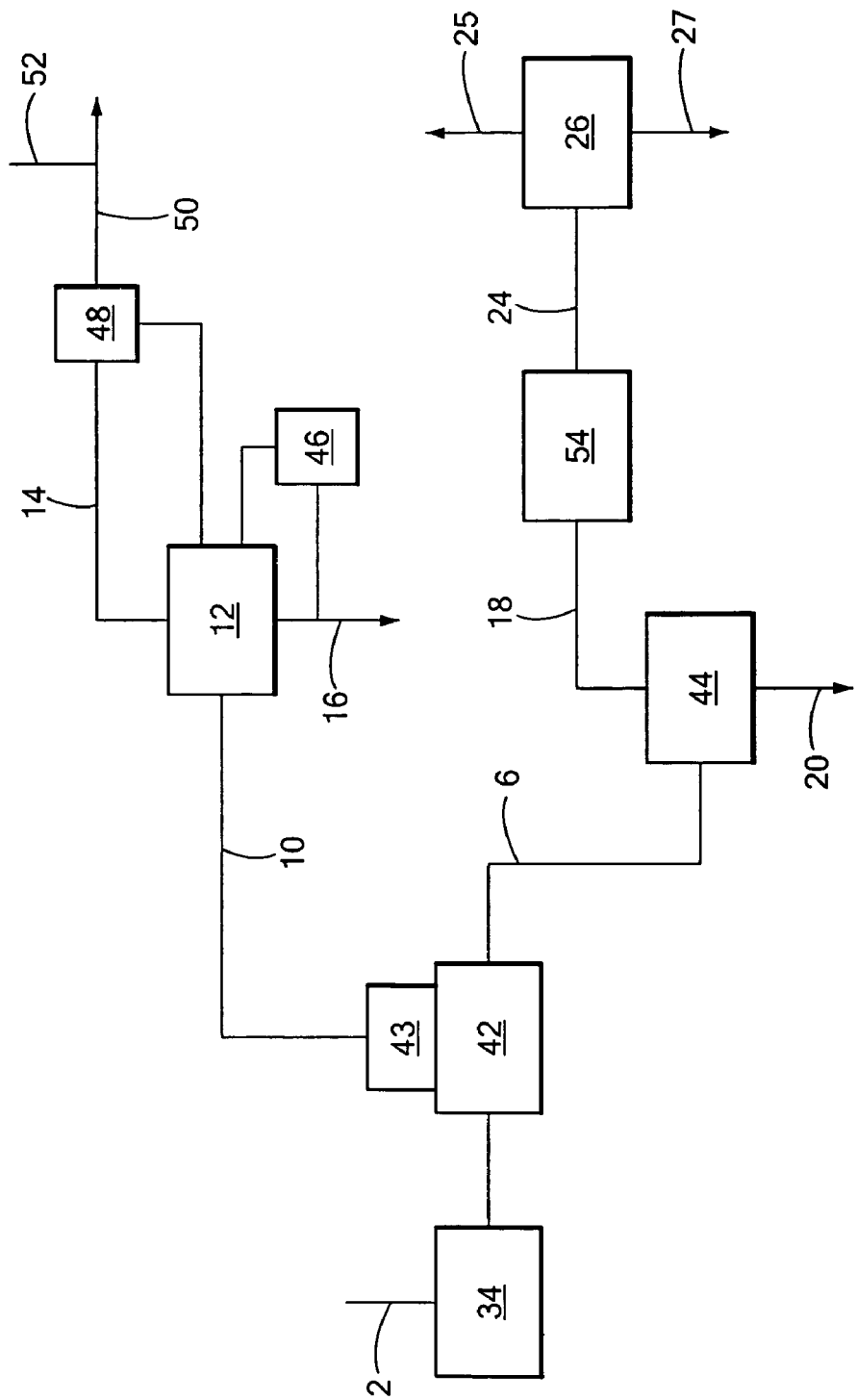
FIG. 5 is a representation of a process of the invention for yielding biodiesel.

FIG. 5 shows one representation of the process of the invention for yielding biodiesel. The feed stream 2 is obtained from a conventional esterification process. The feed stream can comprise mono-alkyl esters, glycerol, alcohol, water, salts and heavies. Preferably, alcohol of the feed stream 2 is methanol such that mono-alkyl esters are methyl esters. The feed stream includes the weight percentages (%) shown in Table 1.

TABLE 1

| Feed Stream | Weight % |
|---|---|
| Methyl Esters | About 30 To 40 |
| Glycerol | About 1 To 5 |
| Water | About 1 To 2 |
| Methanol | About 50 To 65 |
| Heavies | About 1 To 4 |
| Salts | About 1 To 2 |

The feed stream 2 is introduced to the preheater means 34 at a temperature from about 80 to 120 degrees Fahrenheit (° F.). The rate of the feed stream 2 is about 40,000 pounds per hour (pph). The preheater means 34 is also provided with heating media to maintain a consistent temperature.

The feed stream 2 is heated by the preheater means 34 to a temperature from about 250 to 275° F. The feed stream 2 can also be maintained at a pressure of from about 100 to 150 pounds per square inch (psi). The feed stream 2 is provided to a first agitated-film evaporator 42 operating at a pressure of about 300 to 760 torr and, preferably, from about 300 to 500 torr. The evaporator 42 can include a film temperature of about 370 to 390° F. Sparge media or gas such as, for example, nitrogen or steam are introduced to the evaporator. Preferably, super heated sparge steam is provided to the evaporator at a rate of about 400 to 800 pph and temperature of about 300 to 350° F. Heating media such as heat transfer oil is provided to the evaporator 42 to enable evaporation. In one embodiment, the evaporator comprises an entrainment separator 43 associated therewith. The vapor stream 10 passes through the entrainment separator 43 prior to entering the distillation column 12. An exemplary entrainment separator can include demister type pads or short rectifying columns.

The evaporator 42 substantially separates methanol and water from the feed stream 2 into the vapor stream 10 by volatility. The first stream 6 departing the evaporator 42 includes salts, glycerol, heavies and methyl esters. As shown, the first stream 6 is fed to a second agitated-film evaporator 44. The second evaporator 44 operates at a pressure of about 4 to 6 torr. The evaporator 44 can also operate at a temperature of about 380 to 420° F. The second agitated-film evaporator 44 is also heated by a heat transfer media. The evaporator substantially separates methyl esters and glycerol from the first stream 6 into a vapor stream 18. Preferably, a residue stream 20 separated via the evaporator 44 comprises salts and heavies. Salts are separated from the first stream 6 at about 400 to 800 pph. Furthermore, heavies are separated from the first stream at about 400 to 1,600 pph.

The distillation column 12 can be operated at a pressure of about 350 to 760 torr and, preferably, 300 to 500 torr. The column 12 substantially separates methanol from water. For example, water exits from the column 12 as a bottoms stream 16. The majority of the bottoms stream 16 can be disposed of as comprising water and trace quantities of methanol. A portion from the bottoms stream is also sent to a reboiler 46, which heats the bottoms stream 16 to a temperature of about 175 to 190° F. The heated bottoms stream also comprises a rate of reboiling from about 800 to 1,600 pph. The stream 14 comprises methanol with about 0.2% or less of water. The rate of the overhead vapor stream 14 is from about 20,000 to 26,000 pph.

The overhead vapor stream 14 is then introduced into a condenser 48 operating at a pressure from about 300 to 500 torr and temperature of about 120 to 150° F. The condenser 48 also provides the column 12 with reflux at a ratio of about 0.7 to 1.0. The condenser 48 then sends a recycle stream 50 of substantially methanol to the esterification process. The recycle stream also comprises a methanol makeup stream 52 such that the stream 50 operates at a temperature of from about 90 to 110° F. and rate of about 20,000 to 26,000 pph. The process of the invention can also comprise a reflux drum associated with the condenser 48.

As shown, the vapor stream 18 is introduced to a condenser 54 operating at a pressure of about 4 to 6 torr and temperature of about 120 to 150° F. The condenser can condense glycerol and methyl esters in the vapor stream to obtain a liquid stream 24 with a temperature of about 80 to 120° F. The condenser 54 also operates at a pressure of from about 3 to 6 torr. The liquid stream 24 from the condenser is then introduced to a centrifuge 26 to produce methyl esters at a rate of from about 12,000 to 16,000 pph and an overall yield of from about 80 to 98.5%. Glycerol is also yielded at a rate from about 400 to 800 pph. The centrifuge 26 separates methyl esters from glycerol in the liquid stream 24 to produce a fuel grade biodiesel. Fatty acid mono-alkyl esters exit the centrifuge in a yield stream 25 and glycerol in a residual stream 27.

The fatty acid methyl ester biodiesel yield comprises fatty acids such as, for example, linoleic, stearic, palmitic and oleic acids. The fuel grade biodiesel from the process in FIG. 5 can meet or exceed those specifications of ASTM D 6751. The process of FIG. 5 can also be a substantially continuous process. For example, the process produces a substantially continuous yield of biodiesel from such sources of oils and fats as, for example, animal fat, waste type grease, algae and vegetable oil. Such a process as shown in FIG. 5 can be modified so that overall production quantities and qualities of methyl ester biodiesel are specific to a particular application. For example, one type of application for the process may emphasize biodiesel yields rather than a biodiesel of exceptional quality.

EXAMPLE II

Figure 6:
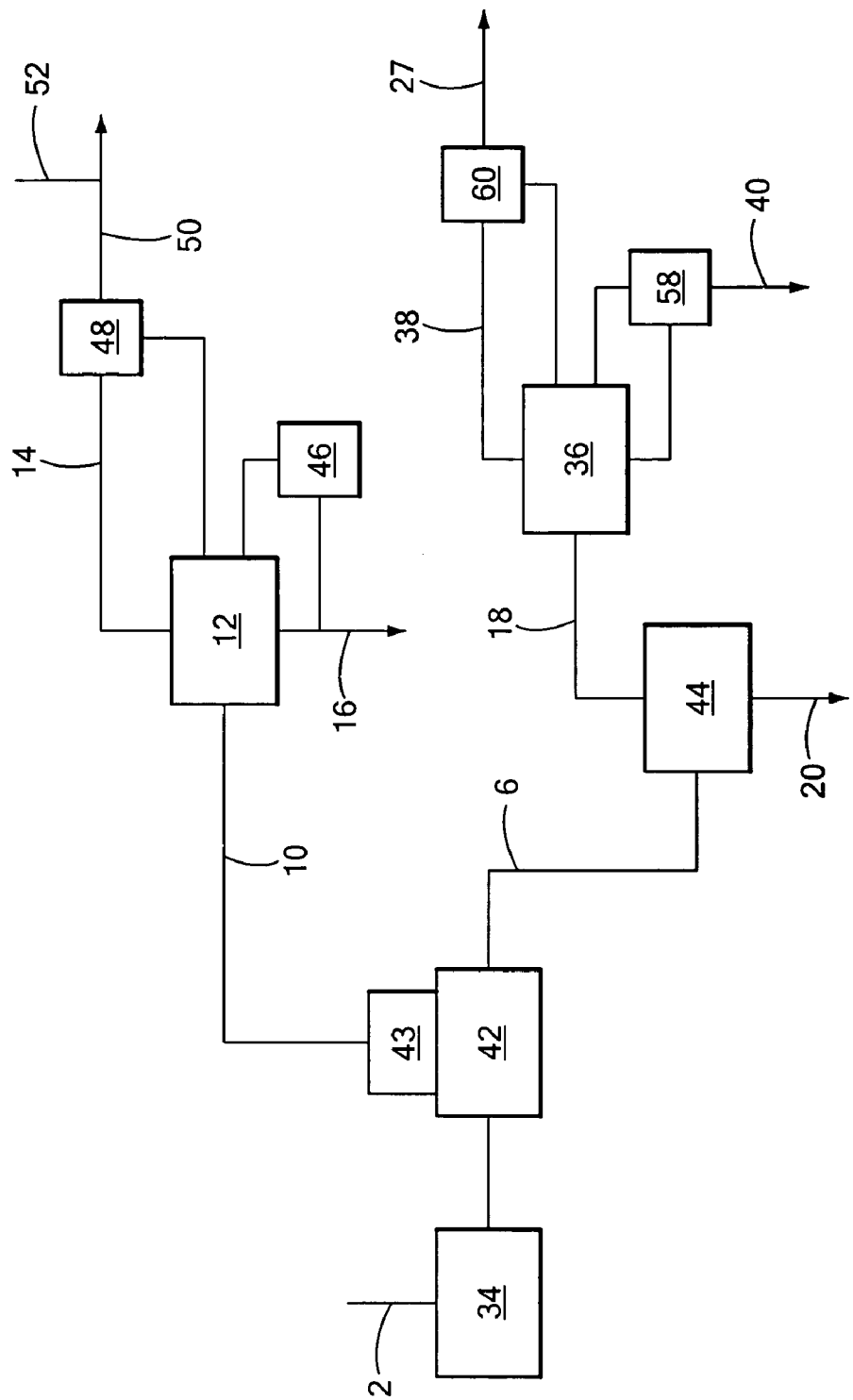
FIG. 6 is a representation of a process of the invention for yielding biodiesel.

FIG. 6 also shows a representation of a process of the invention for yielding biodiesel. The feed stream 2 is obtained from a conventional esterification process. The feed stream can comprise mono-alkyl esters, glycerol, alcohol, water, salts and heavies. Preferably, alcohol present in the stream 2 is methanol such that mono-alkyl esters are methyl esters. The feed stream 2 includes the weight % shown in Table 2.

TABLE 2

| Feed Stream | Weight % |
|---|---|
| Methyl Esters | About 30 To 40 |
| Glycerol | About 1 To 5 |
| Water | About 1 To 2 |
| Methanol | About 50 To 65 |
| Heavies | About 1 To 4 |
| Salts | About 1 To 2 |

The feed stream 2 is introduced to the preheater means 34 at a temperature from about 80 to 120 degrees ° F. The rate of the feed stream 2 is about 40,000 pph. The preheater means 34 is also provided with heating media in order to maintain a consistent temperature.

The feed stream 2 is heated by the preheater means 34 to a temperature from about 250 to 275° F. The feed stream 2 can also be maintained at a pressure of from about 100 to 150 psi. The feed stream 2 is provided to a first agitated-film evaporator 42 operating at a pressure of from about 300 to 760 torr and, preferably, from about 300 to 500 torr. The evaporator 42 can include a film temperature of about 370 to 390° F. Sparge media or gas such as, for example, nitrogen or steam are introduced to the evaporator 42. Preferably, super heated sparge steam is provided to the evaporator at a rate of about 400 to 800 pph and temperature of about 300 to 350° F. Heating media such as heat transfer oil is also provided to the evaporator 42 to enable evaporation. In one embodiment, the evaporator 42 comprises an entrainment separator 43 associated therewith. The vapor stream 10 passes through the entrainment separator 43 prior to entering the distillation column 12. An exemplary entrainment separator can include demister type pads or short rectifying columns.

The evaporator 42 substantially separates methanol and water from the feed stream 2 into the vapor stream 10 by volatility. The first stream 6 departing the evaporator 42 includes salts, glycerol, heavies and methyl esters. As shown, the first stream 6 is provided to a second agitated-film evaporator 44. A second evaporator 44 operates at a pressure of about 4 to 6 torr. The evaporator 44 can also operate at a temperature of about 380 to 420° F. The second agitated-film evaporator 44 is also heated by a heat transfer media. The evaporator substantially separates methyl esters and glycerol from the first stream 6 into a vapor stream 18. Preferably, a residue stream 20 separated via the evaporator 44 comprises salts and heavies. Salts are separated from the first stream 6 at about 400 to 800 pph. Furthermore, heavies are separated from the first stream at about 400 to 1,600 pph.

The distillation column 12 can be operated at a pressure of about 350 to 760 torr and, preferably, 300 to 500 torr. The column 12 substantially separates methanol from water. For example, water exits from the column 12 as a bottoms stream 16. The majority of the bottoms stream 16 can be disposed of as comprising water and trace quantities of methanol. A portion from the bottoms stream is also sent to a reboiler 46, which heats the bottoms stream 16 to a temperature of about 175 to 190° F. The heated bottoms stream also comprises a rate of reboiling from about 800 to 1,600 pph. The stream 14 comprises methanol with about 0.2% or less of water. The rate of the overhead vapor stream 14 is from about 20,000 to 26,000 pph.

The overhead vapor stream 14 is then introduced into a condenser 48 operating at a pressure from about 300 to 500 torr and temperature of about 120 to 150° F. The condenser 48 also provides the column 12 with reflux at a ratio of about 0.7 to 1.0. The condenser 48 then sends a recycle stream 50 of substantially methanol to the esterification process. The recycle stream also comprises a methanol makeup stream 52 such that the stream 50 operates at a temperature of from about 90 to 110° F. and rate of about 20,000 to 26,000 pph. The process of the invention can also comprise a reflux drum associated with the condenser 48.

FIG. 6 shows the vapor stream 18 from the evaporator 44 introduced into the distillation column 36. The column 36 can be operated at a pressure of about 4 to 6 torr. The column 36 substantially separates fatty acid methyl esters from glycerol. For example, methyl esters exit from the column 36 as a bottoms stream 40. The bottoms stream 40 is also sent to a reboiler 58, which reboils the bottoms stream 40. A portion of methyl esters exits the reboiler 58 at a temperature from about 350 to 400° F. The methyl esters yield rate is from about 12,000 to 16,000. Moreover, a methyl esters yield is from about 80 to 98.5%. The fatty acid methyl esters comprise a fuel grade biodiesel.

The overhead vapor stream 38 of the distillation column 36 comprises glycerol. The stream 38 is introduced to a condenser 60 operating at a pressure of about 4 to 6 torr and temperature from about 100 to 120° F. The condenser 60 provides the column 36 with reflux at a ratio of about 4.0 to 8.0 and, preferably, about 5.0. Moreover, the condenser 60 provides a residual stream 27 of glycerol from about 400 to 800 pph at a temperature of about 100 to 120° F. A process of the invention can also comprise a reflux drum associated with the condenser 60. Glycerol from the stream 27 can be used for any particular type of application such as, for example, cosmetic and pharmaceutical applications.

The fatty acid methyl ester biodiesel yield comprises fatty acids such as, for example, linoleic, stearic, palmitic and oleic acids. The fuel grade biodiesel from the process in FIG. 6 can meet or exceed those specifications of ASTM D 6751. The process of FIG. 6 can also be a substantially continuous process. For example, the process produces a substantially continuous yield of biodiesel from such sources of oils and fats as, for example, animal fat, waste type grease, algae and vegetable oil. Such a process as shown in FIG. 6 can be modified so that overall production quantities and qualities of methyl ester biodiesel are specific to a particular application. For example, one type of application for the process may emphasize biodiesel yields rather than a biodiesel of exceptional quality.

While the present invention has been described herein in conjunction with a preferred embodiment, a person with ordinary skill in the art, after reading the foregoing specification, can effect changes, substitutions of equivalents and other types of alterations to the process as set forth herein. Each embodiment described above can also have included or incorporated therewith such variations as disclosed in regard to any or all of the other embodiments. Thus, it is intended that protection granted by Letter Patent hereon be limited in breadth and scope only by definitions contained in the appended claims and any equivalents thereof.

What is claimed is:

1. A process for yielding biodiesel, the process comprising:
providing a feed stream, wherein the feed stream comprises mono-alkyl esters, glycerol, alcohol and salts;
substantially separating alcohol of the feed stream to yield a first stream comprising mono-alkyl esters, glycerol and salts, wherein separation is by volatility;
substantially separating salts of the first stream to yield a vapor stream comprising mono-alkyl esters and glycerol, wherein separation is by volatility; and substantially separating glycerol from the vapor stream to yield a biodiesel comprising mono-alkyl esters.

2. The process of claim 1, wherein the biodiesel is fuel grade biodiesel.

3. The process of claim 1, wherein mono-alkyl esters from the vapor stream are substantially condensed prior to separation from glycerol.

4. The process of claim 1, wherein mono-alkyl esters from the vapor stream are substantially condensed during separation from glycerol.

5. The process of claim 1, the process further comprising prior to said step of providing:
substantially reacting triglycerides with alcohol, wherein reaction is by esterification.

6. The process of claim 5, wherein triglycerides are comprised in a feed source selected from the group consisting of vegetable oil, animal fat, waste type greases and combinations thereof.

7. The process of claim 5, wherein esterification occurs in the presence of a catalyst.

8. The process of claim 5 or 7, wherein esterification yields a product stream comprising glycerol, mono-alkyl esters, salts and alcohol.

9. The process of claim 8, wherein the feed stream is obtained from the product stream.

10. The of claim 7, the process further comprising:
substantially separating water present in the feed source prior to esterification.

11. The process of claim 10, wherein separation of water is by volatility.

12. The process of claim 10, wherein separation of water occurs in an evaporator.

13. The process of claim 10, wherein separation of water occurs in an agitated-film evaporator.

14. The process of claim 1, wherein separation of alcohol from the feed stream occurs in an evaporator.

15. The of claim 1, wherein separation of alcohol from the feed stream occurs in an agitated-film evaporator.

16. The process of claim 1, wherein separation of salts from the feed stream occurs in an evaporator.

17. The process of claim 1, wherein separation of salts from the feed stream occurs in an agitated-film evaporator.

18. The process of claim 1, wherein the process is substantially continuous.

19. A process for yielding biodiesel, the process comprising:
providing a feed stream, wherein the feed stream comprises mono-alkyl esters, glycerol, alcohol and salts;
substantially separating alcohol of the feed stream to yield a first stream comprising mono-alkyl esters, glycerol and salts, wherein separation is by volatility;
substantially separating salts of the first stream to yield a vapor stream comprising mono-alkyl esters and glycerol, wherein separation is by volatility;
substantially condensing mono-alkyl esters and glycerol of the vapor stream to yield a liquid stream; and
substantially separating glycerol from the liquid stream to yield a biodiesel comprising mono-alkyl esters.

20. The process of claim 18, wherein separation of mono-alkyl esters from glycerol is by gravity.

21. The process of claim 20, wherein separation of mono-alkyl esters from glycerol occurs in a centrifuge.

22. The process of claim 21, wherein the process is substantially continuous.

23. A process for yielding biodiesel, the process comprising:
providing a feed stream, wherein the feed stream comprises mono-alkyl esters, glycerol, alcohol and salts;
substantially separating alcohol of the feed stream to yield a first stream comprising mono-alkyl esters, glycerol and salts, wherein separation is by volatility;
substantially separating salts of the first stream to yield a vapor stream comprising mono-alkyl esters and glycerol, wherein separation is by volatility; and
substantially separating glycerol from the vapor stream to yield a liquid stream, wherein separation is by substantially condensing mono-alkyl esters.

24. The process of claim 23, wherein the liquid stream comprises a biodiesel.

25. The process of claim 23, wherein the liquid stream comprises a biodiesel, the biodiesel comprising mono-alkyl esters.

26. The process of claim 24 or 25, wherein the biodiesel is fuel grade biodiesel.

27. The process of claim 23, wherein separation of mono-alky esters from glycerol occurs in a column.

28. A process for yielding biodiesel, the process comprising:
substantially reacting triglycerides with alcohol to yield a feed stream comprising alcohol, glycerol, mono-alkyl esters, water and salts, wherein reaction is by esterification;
substantially separating alcohol and water of the feed stream to yield a first stream comprising mono-alkyl esters, glycerol and salts, wherein separation is by volatility;
substantially separating salts of the first stream, to yield a vapor stream comprising mono-alkyl esters and glycerol, wherein separation is by volatility; and
substantially separating glycerol from the vapor stream to yield a biodiesel comprising mono-alkyl esters.

29. The process of claim 28, wherein the biodiesel is fuel grade biodiesel.

30. The process of claim 28, wherein mono-alkyl esters from the vapor stream are substantially condensed prior to separation from glycerol.

31. The process of claim 30, wherein separation of substantially condensed mono-alkyl esters is by gravity.

32. The process of claim 31, wherein separation of substantially condensed mono-alkyl esters occurs in a centrifuge.

33. The process of claim 28, wherein mono-alkyl esters from the vapor stream are substantially condensed during separation from glycerol.

34. The process of claim 33, wherein mono-alkyl esters from the vapor stream are substantially condensed in a column.

35. The process of claim 28, wherein separation of alcohol and water from the feed stream occurs in an evaporator.

36. The process of claim 35, wherein separation of alcohol and water from the feed stream occurs in an agitated-film evaporator.

37. The process of claim 28, wherein separation of salts from the feed stream occurs in an evaporator.

38. The process of claim 37, wherein separation of salts from the feed stream occurs in an agitated-film evaporator.

39. The process of claim 1, wherein the process is substantially continuous.

40. The process of claim 28, wherein said triglycerides are from a feed source.

41. The process of claim 40, the process further comprising:
   substantially separating water from the feed source prior to esterification.

42. The process of claim 41, wherein separation of water is by volatility.

43. The process of claim 42, wherein separation of water occurs in an evaporator.

44. The process of claim 42, wherein separation of water occurs in an agitated-film evaporator.

* * * * *

UNITED STATES PATENT AND TRADEMARK OFFICE
CERTIFICATE OF CORRECTION

| | |
|---|---|
| PATENT NO. | : 7,528,272 B2 |
| APPLICATION NO. | : 11/235673 |
| DATED | : May 5, 2009 |
| INVENTOR(S) | : Perry Alasti |

It is certified that error appears in the above-identified patent and that said Letters Patent is hereby corrected as shown below:

Column 15, line 26, claim 10, "The of" should read --The process of--;

Column 15, line 37, claim 15, "The of" should read --The process of--; and

Column 16, line 33, claim 28, "stream," should read --stream--.

Signed and Sealed this

First Day of December, 2009

David J. Kappos
*Director of the United States Patent and Trademark Office*